(12) United States Patent
Blythe et al.

(10) Patent No.: US 7,659,309 B2
(45) Date of Patent: Feb. 9, 2010

(54) POLYMORPHIC FORMS OF (1-{3-[3-(4-CYANO-3-METHOXY-PHENYL) UREIDO]-PHENYL}-ETHYL)-CARBAMIC ACID-2-CYANO-1-ETHYL-ETHYL ESTER

(75) Inventors: Todd Blythe, Georgetown, MA (US); Philip Nyce, Millbury, MA (US); Yong Cui, Foster City, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 578 days.

(21) Appl. No.: 11/086,142

(22) Filed: Mar. 22, 2005

(65) Prior Publication Data

US 2005/0239879 A1    Oct. 27, 2005

Related U.S. Application Data

(60) Provisional application No. 60/555,553, filed on Mar. 23, 2004.

(51) Int. Cl.
*A61K 31/27* (2006.01)
*A61K 31/23* (2006.01)
*C07C 255/51* (2006.01)

(52) U.S. Cl. .................. 514/485; 514/552; 558/410; 558/417

(58) Field of Classification Search ............... 558/417; 514/522

See application file for complete search history.

(56) References Cited

U.S. PATENT DOCUMENTS 6,498,178 B2 *  12/2002  Stamos et al. ............... 514/374
2002/0111378 A1  8/2002  Stamos et al. ............... 514/473

OTHER PUBLICATIONS

Jain J. et al., "Characterization of Pharmacological Efficacy of VX-148, A New, Potent Immunosuppressive Inosine 5'—Monophosphate Dehydrogenase Inhibitor", Journal of Pharmacology and Experimental Therapeutics, American Society for Pharmacology and, US, 302(3): 1272-1277 (2002).
Mino R. Caira, "Crystalline Polymorphism of Organic Compounds", Topics in Current Chemistry, 198: 163-208 (1998).

* cited by examiner

*Primary Examiner*—James O Wilson
*Assistant Examiner*—Ebenezer Sackey
(74) *Attorney, Agent, or Firm*—Michael C. Badia

(57) ABSTRACT

The present invention relates to polymorphic forms of (1-{3-[3-(4-cyano-3-methoxy-phenyl)ureido]-phenyl}-ethyl)-carbamic acid-2-cyano-1-ethyl-ethyl ester, processes therein, pharmaceutical compositions thereof, and uses therewith.

11 Claims, 6 Drawing Sheets

POLYMORPHIC FORMS OF (1-{3-[3-(4-CYANO-3-METHOXY-PHENYL) UREIDO]-PHENYL}-ETHYL)-CARBAMIC ACID-2-CYANO-1-ETHYL-ETHYL ESTER

CROSS REFERENCE TO RELATED APPLICATIONS

This application claims the benefit under 35 U.S.C. §119 of U.S. Provisional Application No. 60/555,553, filed Mar. 23, 2004 and entitled "Polymorphic Forms of (1-{3-[3-(4-cyano-3-methoxy-phenyl)ureido]-phenyl}-ethyl)-carbamic acid-2-cyano-1-ethyl-ethyl ester", the entire contents of which is hereby incorporated by reference.

TECHNICAL FIELD OF THE INVENTION

The present invention relates to polymorphic forms of (1-{3-[3-(4-cyano-3-methoxy-phenyl)ureido]-phenyl}-ethyl)-carbamic acid-2-cyano-1-ethyl-ethyl ester, processes therein, pharmaceutical compositions thereof, and methods therewith.

BACKGROUND OF THE INVENTION

The present invention relates to polymorphic forms of (1-{3-[3-(4-cyano-3-methoxy-phenyl)ureido]-phenyl}-ethyl)-carbamic acid-2-cyano-1-ethyl-ethyl ester having the structure below (hereinafter "Compound 1"):

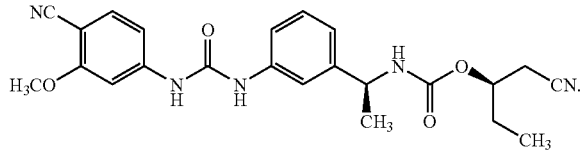

The present invention also relates to processes to prepare polymorphic forms of Compound 1.

Compound 1 is a potent IMPDH inhibitor useful in treating IMPDH-mediated diseases. Compound 1, compositions thereof, and methods therewith are disclosed in U.S. Pat. No. 6,498,178 B2 (hereinafter "the '178 patent"), the entire disclosure whereof is incorporated herein by reference.

SUMMARY OF THE INVENTION

The present invention provides six polymorphic forms of Compound 1, namely, Form A, Form B, Form C, Form D, Form E, and Form F. The present invention also relates to processes for making these polymorphic forms. The invention also relates to the use of these polymorphic forms in therapeutic methods and in the preparation of pharmaceutical compositions comprising such polymorphic forms. The present invention also relates to an amorphous form of Compound 1, and processes for producing such an amorphous form.

DETAILED DESCRIPTION OF THE INVENTION

The term "suitable" as used herein, describes solvent, temperature, filtrate, agitation, solution, medium, quantity, period of time, etc. Such suitable solvents, temperature, filtrate, agitation, solution, medium, quantity, period of time, etc. are readily known to one of skill in the art.

Figure 1:
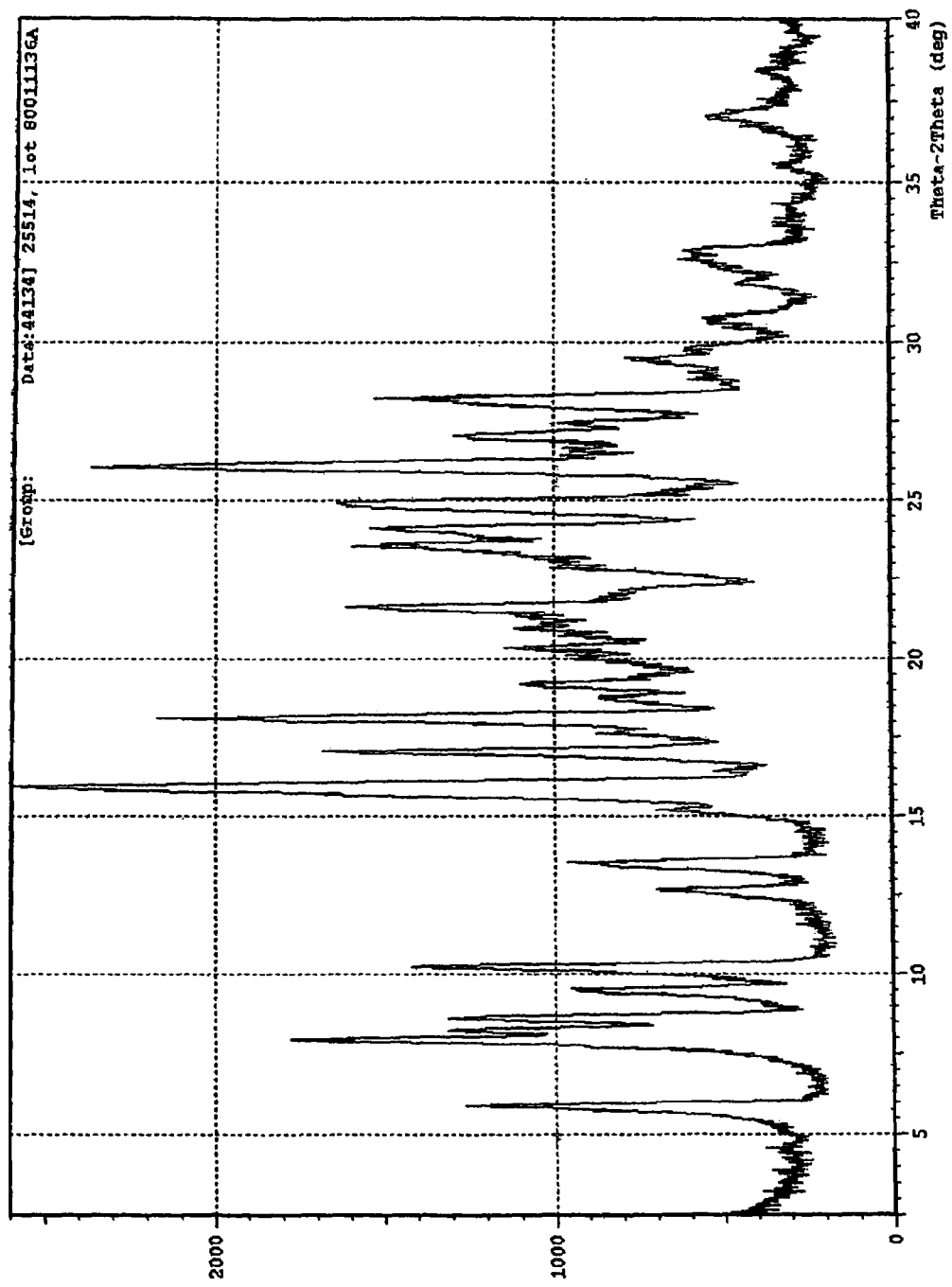
FIG. 1 is an X-ray powder diffraction pattern of Form A.

According to one embodiment, the present invention provides a polymorphic Form A of Compound 1 (hereinafter "Form A") characterized by one or more peaks at about 5.76, 7.82, 8.10, 10.08, and 15.73 degrees 2θ in an X-ray powder diffraction pattern obtained using Cu K alpha radiation. According to another embodiment, the invention provides Form A characterized by an X-ray powder diffraction pattern obtained using Cu K alpha radiation substantially similar to FIG. 1.

According to another embodiment, Form A is characterized by a melting point temperature of between about 148° C. to about 156° C.

According to another embodiment, the present invention provides a process for preparing Form A, as exemplified hereinbelow.

According to another embodiment, the present invention provides a pharmaceutical composition comprising Form A and a pharmaceutically acceptable carrier or adjuvant.

According to another embodiment, the present invention provides a method of formulating a pharmaceutical composition comprising an amorphous form of Compound 1, comprising the steps of:
  (i) converting Form A to an amorphous form; and
  (ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form A or a pharmaceutical composition comprising Form A.

According to another embodiment, the present invention provides a process for preparing a polymorph of Form A, said process at least one of the following steps:
a) dissolving 1-{3-[3-(4-cyano-3-methoxy-phenyl)ureido]-phenyl}-ethyl)-carbamic acid-2-cyano-1-ethyl-ethyl ester in a suitable solvent with suitable agitation at a suitable temperature to give a suitable solution;
b) filtering said solution through a suitable medium at a suitable temperature to give a suitable filtrate;
c) cooling said filtrate to about room temperature;
d) seeding said filtrate with a suitable quantity of Form A;
e) concentrating said filtrate under a suitable reduced pressure and suitable temperature to about one-third the original volume to give a slurry;
f) agitating said slurry for a suitable period of time at a suitable temperature;
g) adding a suitable amount of a suitable solvent at a suitable temperature to generate a suitable solution;
h) adding about one volume of a suitable solvent over a suitable period of time, at a suitable temperature with agitation to generate a slurry;
i) cooling said slurry to about room temperature and agitating for a suitable period of time;
j) isolating the product by filtration or centrifugation;
k) rinsing said product with about a 1:1 mixture of suitable solvents; and l) drying said product at a suitable temperature under a suitable reduced pressure for a suitable period of time to constant weight.

According to another embodiment, the present invention provides a process for preparing a polymorph of Form A comprising the following steps. A suspension of Form B in distilled water was kept stirring or left unstirred at room temperature for 5-10 days. The product was filtered or centrifuged, washed with distilled water (3×) and then vacuum-dried at room temperature to produce Form A.

In another embodiment, stirring and/or increasing the temperature accelerates the transformation rate of Form B to Form A. In another embodiment, the temperature ranges from about 20° C. to about 100° C.

According to another embodiment, the present invention provides a process for preparing a polymorph of Form A comprising the following steps. A suspension of Form B in a 0.001-0.1% weight to volume surfactant solution of SLS was kept stirring or left unstirred at room temperature for 5-10 days. The product was filtered or centrifuged, washed with distilled water (3×) and then vacuum-dried at room temperature to produce Form A.

In one embodiment, the surfactants comprise anionic surfactants. In another embodiment, the anionic surfactants comprise carboxylate, sulfonate, or sulfate ions. In another embodiment, the sulfonate containing anionic surfactants comprise long alkyl chain sulfonates such as sodium bis-(2-ethylhexyl)sulfosuccinates (Aerosol OT or docusate sodium) and alkyl aryl sulfonates such as sodium dodecylbenzene sulfonate. In yet another embodiment, the sulfate containing anionic surfactants comprise alkyl sulfates such as sodium lauryl sulfate.

In one embodiment, the surfactants comprise nonionic surfactants. In another embodiment, the nonionic surfactants comprise long-chain fatty acids or steroidal alcohols as the non-polar groups. In another embodiment, the polar groups comprise polyoxyethylene or polyethylene glycol groups linked with one of their alcohol groups through an ether linkage. In yet another embodiment, the polyoxyethylene or polyethylene glycol groups comprise polyoxyethylene sorbitan fatty acid esters such as polysorbates and Tweens; polyoxyethylene alkyl esters such as Brijs or Solutol HS15; polyoxyethylene castor oil derivatives such as polyoxyle 35 castor oil, polyoxyl 40 hydrogenated castor oil, and polyoxyl 60 hydrogenated castor oil; polyoxyethylene stearates or other fatty acid esters such as Polyoxyl 40 stearate and polyoxyl 50 stearate (Myrjs); polyethylene fatty acid esters such as PEG400 monostearate and propylene glycol monocaprylate (Capryol); d-alpha tocopheryl polyethylene glycol 1000 succinate (Vitamin E TPGS); caprylocaproyl macrogolglycerides (Labrasol), glycerol and PEG1500 esters of fatty acid (Gellucire).

In another embodiment, said surfactants comprise a hydrophile-lipohile balance (HLB) number of about 4 or higher.

In another embodiment, said surfactants comprise a hydrophile-lipohile balance (HLB) number of about 8 or higher.

In another embodiment, said surfactants comprise a hydrophile-lipohile balance (HLB) number of about 10 or higher.

In another embodiment, stirring and/or increasing the temperature accelerates the transformation rate of Form B to Form A. In another embodiment, the temperature ranges from about 20° C. to about 100° C.

According to one embodiment, the present invention provides a polymorphic Form B of Compound 1, characterized by one or more peaks at about 11.72, 14.57, 18.25, 22.40, and 27.72 degrees 2θ in an X-ray powder diffraction pattern obtained using Cu K alpha radiation.

Figure 2:
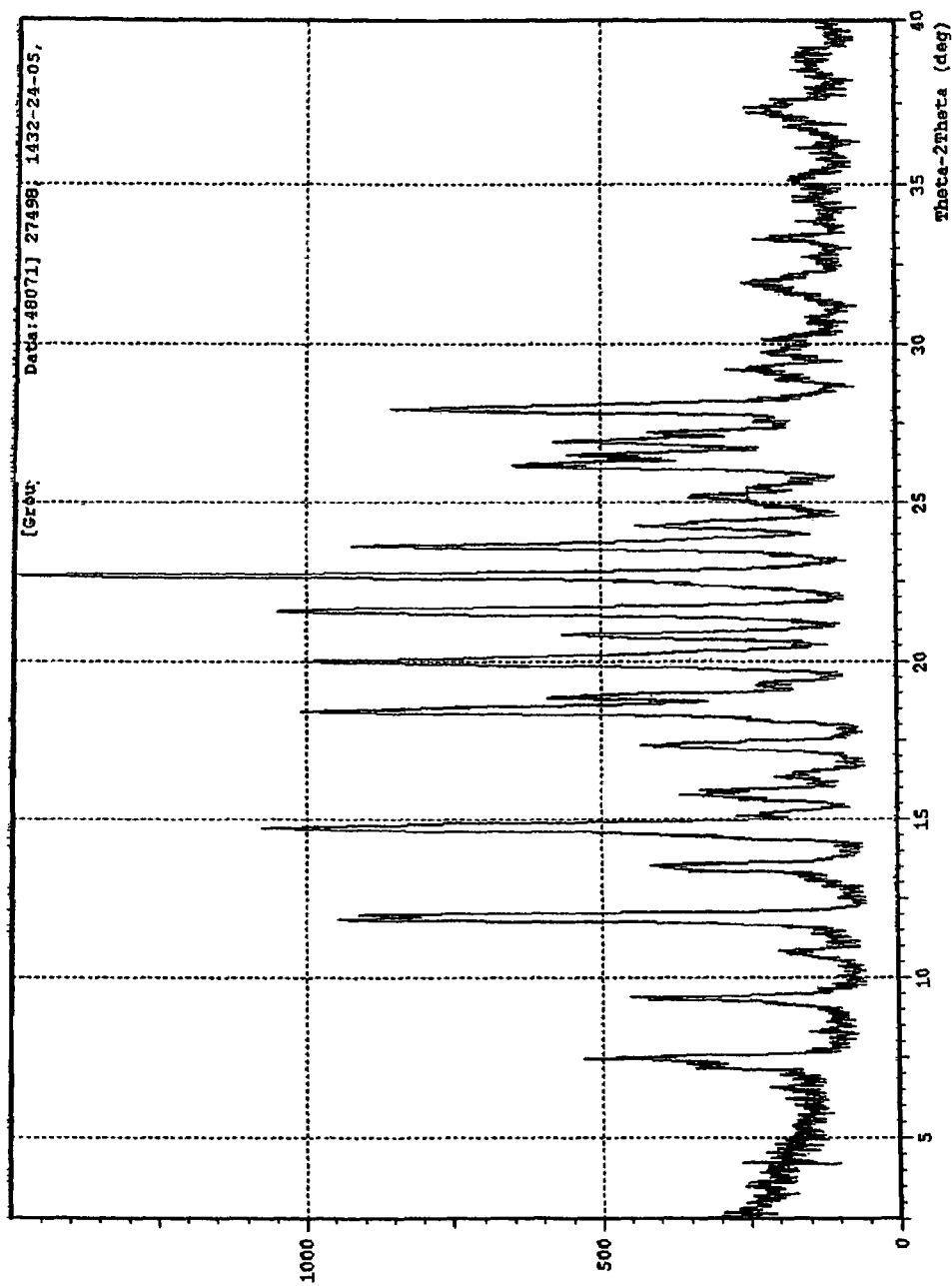
FIG. 2 is an X-ray powder diffraction pattern of Form B.

According to another embodiment, the invention provides Form B characterized by an X-ray powder diffraction pattern obtained using Cu K alpha radiation substantially similar to FIG. 2.

According to another embodiment, Form B is characterized by a melting point temperature of about 131° C.

According to another embodiment, Form B shows enhanced bioavailability.

According to another embodiment, the present invention provides a process for preparing Form B, as exemplified hereinbelow.

According to another embodiment, the present invention provides a pharmaceutical composition comprising Form B and a pharmaceutically acceptable carrier or adjuvant.

According to another embodiment, the present invention provides a method of formulating a pharmaceutical composition comprising an amorphous form of Compound 1, comprising the steps of:
  (i) converting Form B to an amorphous form; and
  (ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form B or a pharmaceutical composition comprising Form B.

According to another embodiment, the present invention provides a process for preparing a polymorph of Form B, said process comprising at least one of the following steps:
a) dissolving 1-{3-[3-(4-cyano-3-methoxy-phenyl)ureido]-phenyl}-ethyl)-carbamic acid-2-cyano-1-ethyl-ethyl ester in a suitable solvent with suitable agitation at a suitable temperature to give a suitable solution;
b) adding a suitable amount of a suitable solvent at a suitable temperature to generate a suitable solution;
c) allowing said solution to cool to about room temperature for a suitable period of time with or without suitable agitation to generate a slurry;
d) agitating said slurry for a suitable period of time;
e) isolating the precipitated product by filtration or centrifugation;
f) rinsing said product with a suitable solvent;
g) suspending said product in a suitable solvent with suitable agitation at a suitable temperature;
h) isolating said product by filtration or centrifugation at a suitable temperature;
i) rinsing said product with about a suitable solvent; and
j) drying said product at a suitable temperature under a suitable reduced pressure for a suitable period of time to constant weight.

Figure 3:
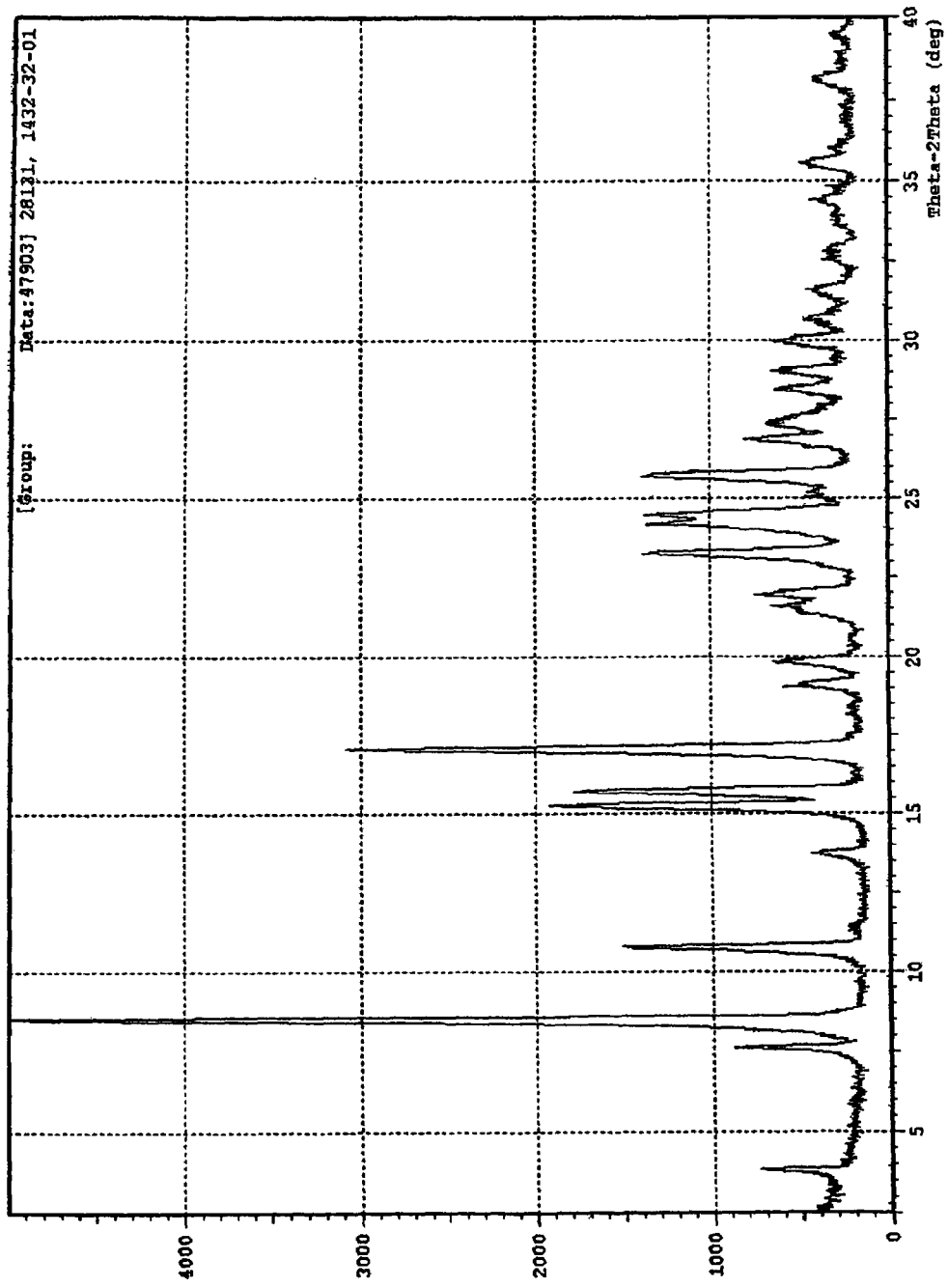
FIG. 3 is an X-ray powder diffraction pattern of Form C.

According to one embodiment, the present invention provides a polymorphic Form C of Compound 1, characterized by one or more peaks at about 3.82, 8.50, 10.74, 15.22, 17.02 degrees 2θ in an X-ray powder diffraction pattern obtained using Cu K alpha radiation. According to another embodiment, the invention provides Form C characterized by an X-ray powder diffraction pattern obtained using Cu K alpha radiation substantially similar to FIG. 3.

According to another embodiment, Form C is characterized by a melting point temperature of about 77° C.

According to another embodiment, the present invention provides a process for preparing Form C, as exemplified hereinbelow.

According to another embodiment, the present invention provides a pharmaceutical composition comprising Form C and a pharmaceutically acceptable carrier or adjuvant.

According to another embodiment, the present invention provides a method of formulating a pharmaceutical composition comprising an amorphous form of Compound 1, comprising the steps of:
(i) converting Form C to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form C or a pharmaceutical composition comprising Form C.

Figure 4:
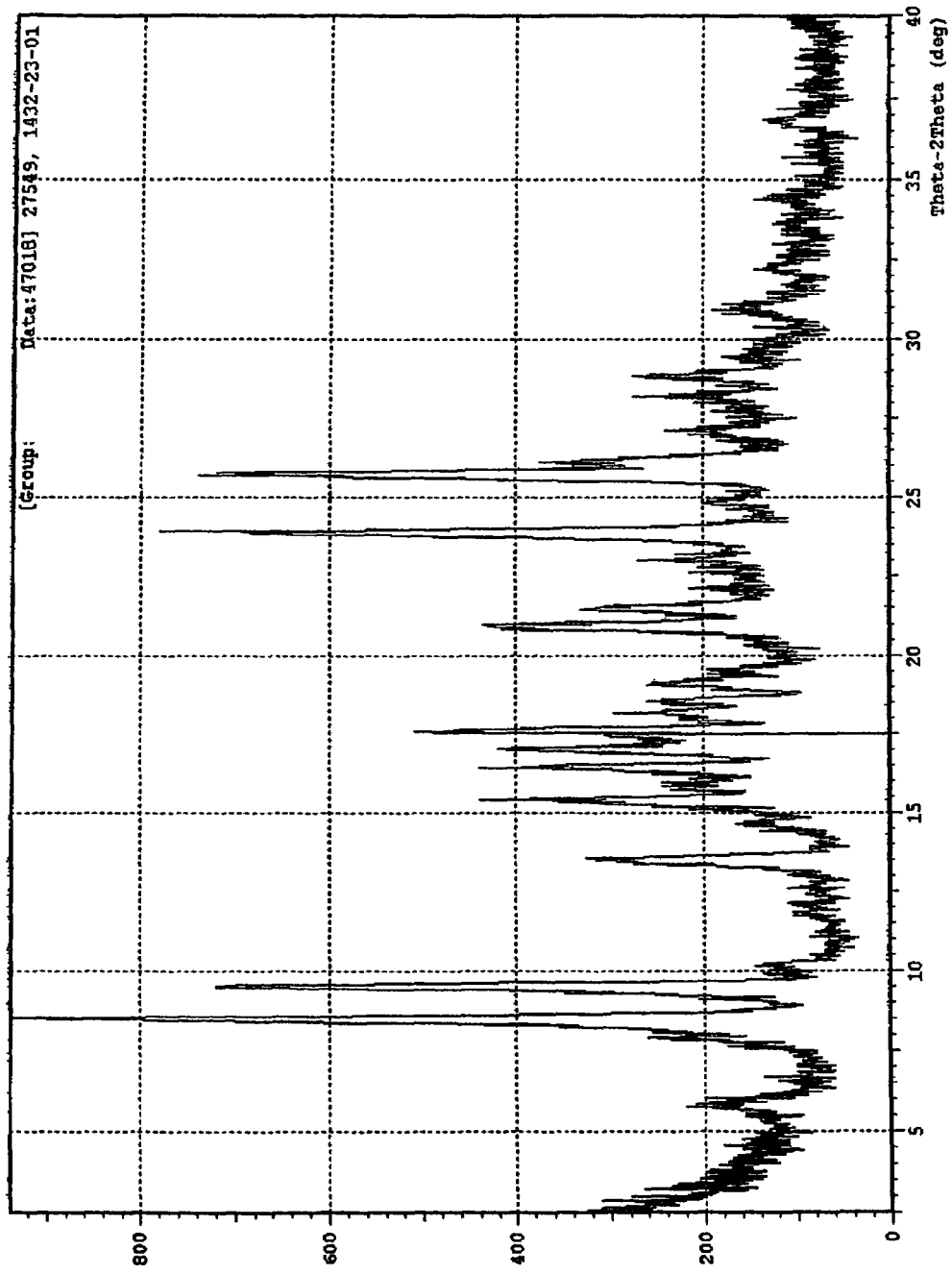
FIG. 4 is an X-ray powder diffraction pattern of Form D.

According to one embodiment, the present invention provides a polymorphic form D characterized by one or more peaks at about 6.06, 9.53, and 23.86 degrees 2θ in an X-ray powder diffraction pattern obtained using Cu K alpha radiation. According to another embodiment, the invention provides Form D characterized by an X-ray powder diffraction pattern obtained using Cu K alpha radiation substantially similar to FIG. 4.

According to another embodiment, the present invention provides a process for preparing Form D, as exemplified hereinbelow.

According to another embodiment, the present invention provides a pharmaceutical composition comprising Form D and a pharmaceutically acceptable carrier or adjuvant.

According to another embodiment, the present invention provides a method of formulating a pharmaceutical composition comprising an amorphous form of Compound 1, comprising the steps of:
(i) converting Form D to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form D or a pharmaceutical composition comprising Form D.

According to another embodiment, the present invention provides a process for preparing a polymorph of Form D, said process comprising at least one of the following steps:
a) dissolving 1-{3-[3-(4-cyano-3-methoxy-phenyl)ureido]-phenyl}-ethyl)-carbamic acid-2-cyano-1-ethyl-ethyl ester in a suitable solvent with suitable agitation at a suitable temperature to give a suitable solution;
b) adding a suitable amount of a suitable solvent at a suitable temperature to generate a suitable solution;
c) allowing said solution to cool to about room temperature for a suitable period of time with or without suitable agitation to generate a slurry;
d) agitating said slurry for a suitable period of time;
e) isolating the precipitated product by filtration or centrifugation;
f) rinsing said product with about a suitable solvent;
g) suspending said product in a suitable solvent with suitable agitation at a suitable temperature;
h) isolating said product by filtration or centrifugation at a suitable temperature;
i) rinsing said product with about a suitable solvent; and
j) drying said product at a suitable temperature under a suitable reduced pressure for a suitable period of time to constant weight.

According to one embodiment, the present invention provides a polymorphic Form E of Compound 1 (hereinafter "Form E") characterized by one or more peaks at about 5.15, 14.76, 20.86, 24.28, 24.94 degrees 2θ in an X-ray powder diffraction pattern obtained using Cu K alpha radiation.

Figure 5:
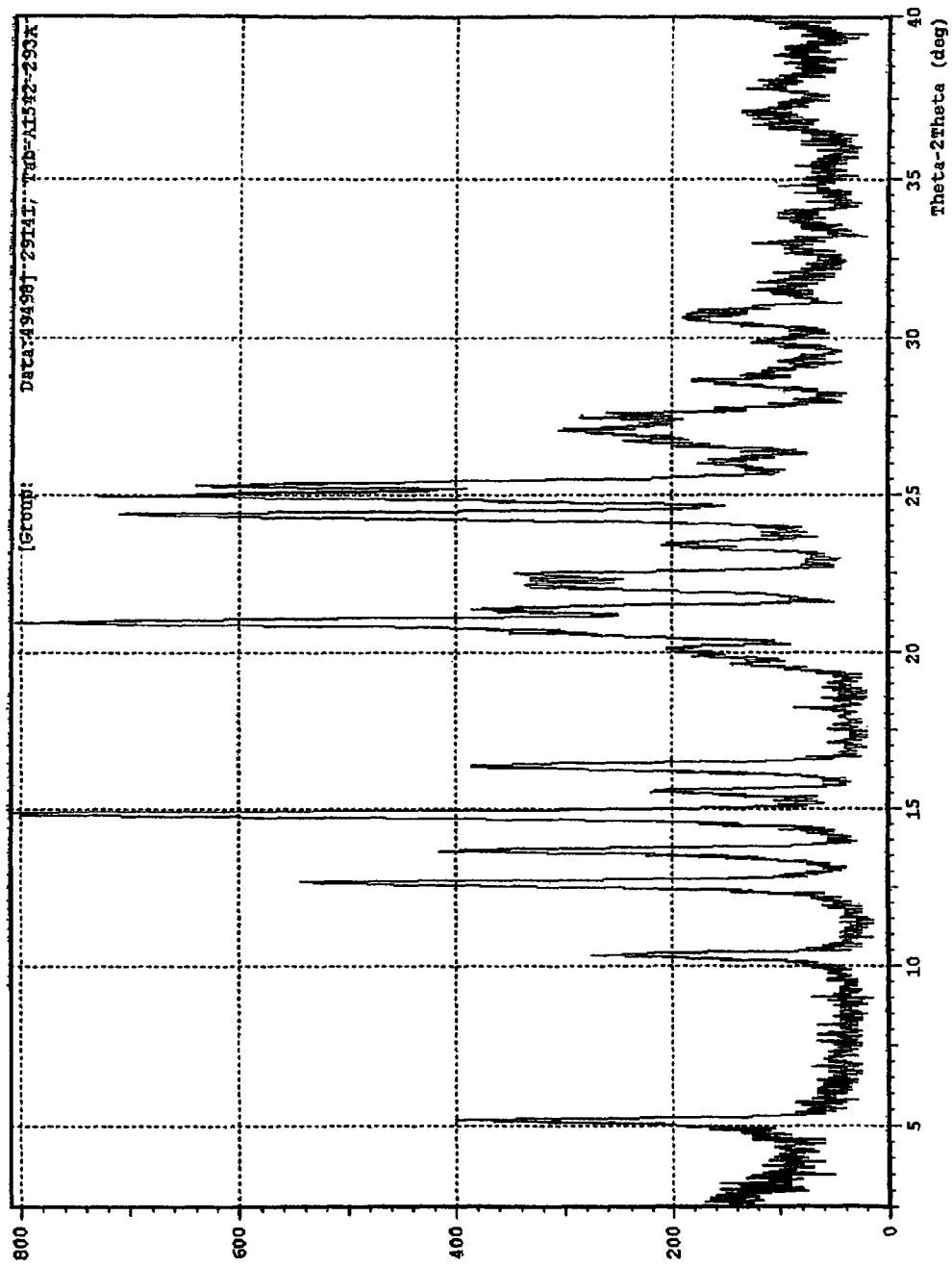
FIG. 5 is an X-ray powder diffraction pattern of Form E.

According to another embodiment, the invention provides Form E characterized by an X-ray powder diffraction pattern obtained using Cu K alpha radiation substantially similar to FIG. 5.

According to another embodiment, Form E is characterized by a melting point temperature of about 151° C.

According to another embodiment, the present invention provides a process for preparing Form E, as exemplified hereinbelow.

According to another embodiment, the present invention provides a process for preparing a polymorph of Form E comprising the following steps. A suspension of Form B in distilled water was kept stirring or left unstirred at room temperature for 5-10 days. The product was filtered or centrifuged, washed with distilled water (3×) and then vacuum-dried at room temperature to produce Form E.

In another embodiment, stirring and/or increasing the temperature accelerates the transformation rate of Form B to Form E. In another embodiment, the temperature ranges from about 20° C. to about 100° C.

According to another embodiment, the present invention provides a process for preparing a polymorph of Form E comprising the following steps. A suspension of Form B in a 0.1% weight to volume surfactant solution of SLS was kept stirring or left unstirred at room temperature for 5-10 days. The product was filtered or centrifuged, washed with distilled water (3×) and then vacuum-dried at room temperature to produce Form E.

In one embodiment, said surfactants comprise anionic surfactants. In another embodiment, the anionic surfactants comprise carboxylate, sulfonate, or sulfate ions. In another embodiment, the sulfonate containing anionic surfactants comprise long alkyl chain sulfonates such as sodium bis-(2-ethylhexyl)sulfosuccinates (Aerosol OT or docusate sodium) and alkyl aryl sulfonates such as sodium dodecylbenzene sulfonate. In yet another embodiment, the sulfate containing anionic surfactants comprise alkyl sulfates such as sodium lauryl sulfate.

In one embodiment, said surfactants comprise nonionic surfactants. In another embodiment, the nonionic surfactants comprise long-chain fatty acids or steroidal alcohols as the non-polar groups. In another embodiment, the polar groups comprise polyoxyethylene or polyethylene glycol groups linked with one of their alcohol groups through an ether linkage. In yet another embodiment, the polyoxyethylene or polyethylene glycol groups comprise polyoxyethylene sorbitan fatty acid esters such as polysorbates and Tweens; polyoxyethylene alkyl esters such as Brijs or Solutol HS15; polyoxyethylene castor oil derivatives such as polyoxyle 35 castor oil, polyoxyl 40 hydrogenated castor oil, and polyoxyl 60 hydrogenated castor oil; polyoxyethylene stearates or other fatty acid esters such as Polyoxyl 40 stearate and polyoxyl 50 stearate (Myrjs); polyethylene fatty acid esters such as PEG400 monostearate and propylene glycol monocaprylate (Capryol); d-alpha tocopheryl polyethylene glycol 1000 succinate (Vitamin E TPGS); caprylocaproyl macrogolglycerides (Labrasol), glycerol and PEG1500 esters of fatty acid (Gellucire).

In another embodiment, said surfactants comprise a hydrophile-lipohile balance (HLB) number of about 4 or higher.

In another embodiment, said surfactants comprise a hydrophile-lipohile balance (HLB) number of about 8 or higher.

In another embodiment, said surfactants comprise a hydrophile-lipohile balance (HLB) number of about 10 or higher.

In another embodiment, stirring and/or increasing the temperature accelerates the transformation rate of Form B to Form E. In another embodiment, the temperature ranges from about 20° C. to about 100° C.

According to another embodiment, the present invention provides a pharmaceutical composition comprising Form E and a pharmaceutically acceptable carrier or adjuvant.

According to another embodiment, the present invention provides a method of formulating a pharmaceutical composition comprising an amorphous form of Compound 1, comprising the steps of:

(i) converting Form E to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form E or a pharmaceutical composition comprising Form E.

Figure 6:
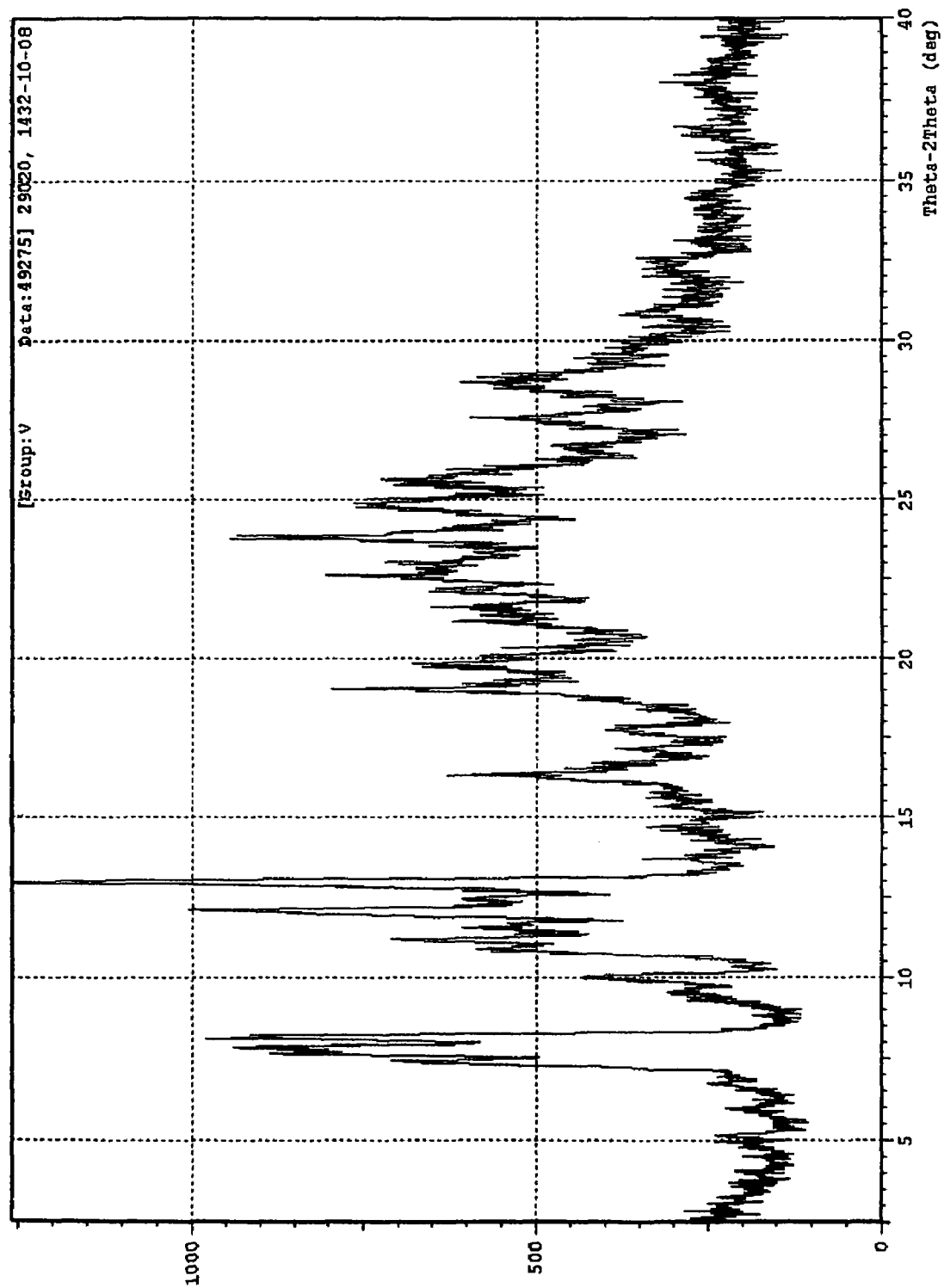
FIG. 6 is an X-ray powder diffraction pattern of Form F.

According to one embodiment, the present invention provides a polymorphic Form F of Compound 1 (hereinafter "Form F") characterized by one or more peaks at about 7.82, 8.16, 12.93, 19.01, 23.83 degrees 2θ in an X-ray powder diffraction pattern obtained using Cu K alpha radiation According to another embodiment, the invention provides Form F characterized by an X-ray powder diffraction pattern obtained using Cu K alpha radiation substantially similar to FIG. 6.

According to another embodiment, the present invention provides a process for preparing Form F, as exemplified hereinbelow.

According to another embodiment, the present invention provides a pharmaceutical composition comprising Form F and a pharmaceutically acceptable carrier or adjuvant.

According to another embodiment, the present invention provides a method of formulating a pharmaceutical composition comprising an amorphous form of Compound 1, comprising the steps of:

(i) converting Form F to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form F or a pharmaceutical composition comprising Form F.

The term "pharmaceutically acceptable carrier or adjuvant" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

When the compositions of this invention comprise a combination of an IMPDH inhibitor of this invention and one or more additional therapeutic or prophylactic agents, such as those disclosed herein, both the IMPDH inhibitor and the additional agent(s) should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

When the compositions of this invention comprise a combination of an IMPDH inhibitor of this invention and one or more additional therapeutic or prophylactic agents, both the compound and the additional agent should be present at dosage levels of between about 10 to 100% and in another embodiment between about 10 to 80% of the dosage normally administered in a monotherapy regimen.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, mizoribine, and interferon including alpha-interferon such as PEG-Intron® and Pegasys®.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) Intron (interferon-alpha 2B, Schering Plough),
(b) Peg-Intron,
(c) Pegasys,
(d) Roferon,
(e) Berofor,
(f) Sumiferon,
(g) Wellferon,
(h) consensus alpha interferon available from Amgen, Inc., Newbury Park, Calif., (i) Alferon;
(j) Viraferon®;
(k) Infergen®.

According to an alternate embodiment, the pharmaceutical compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

In another embodiment, the compositions of this invention additionally comprise another anti-viral agent, including an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin (and the combination therapy of ribavirin and pegylated interferon [Rebetrol®]), d4T, ddI, AZT, amprenavir, fos-amprenavir, acyclovir, NS3-NS4A protease inhibitors such as those disclosed in PCT publication No. WO 02/018369, amantadine, cytovene, ganciclovir, ritonivir, trisodium phosphonoformate, and telbivudine; other inhibitors of hepatitis C proteases (NS2-NS3 inhibitors and NS3-NS4A inhibitors); inhibitors of other targets in the HCV life cycle, including but not limited to, helicase and polymerase inhibitors; inhibitors of internal ribosome entry; and broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof).

In one embodiment, the compositions of this invention additionally comprise another agent, including a cytochrome P-450 inhibitor. Such cytochrome P-450 inhibitors include, but are not limited to, ritonavir. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the IMPDH inhibitor may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. For preferred dosage forms of ritonavir, see U.S. Pat. No 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P450 monooxygenase activity are known (see U.S. Pat. No. 6,037,157 and Yun, et al. *Drug Metabolism & Disposition*, vol. 21, pp. 403-407 (1993).

According to yet another alternate embodiment, the pharmaceutical compositions of this invention may additionally comprise an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

According to one embodiment, the term "IMPDH-mediated disease" as used herein includes immune system related diseases such as transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

According to another embodiment, the term "IMPDH-mediated disease" as used herein includes viral diseases such as DNA and RNA viral diseases caused by infection for example, by orthomyxoviruses (influenza viruses types A and B), paramyxoviruses (respiratory syncytial virus (RSV), sub-acute sclerosing panencephalitis (SSPE) virus) measles and parainfluenza type 3), herpesviruses (HSV-1, HSV-2, HHV-6, HHV-7, HHV-8, Epstein Barr Virus (EBV), cytomegalovirus (HCMV) and varicella zoster virus (VZV)), retroviruses (HIV-1, HIV-2, HTLV-1, HTLV-2), flavi- and pestiviruses (yellow fever virus (YFV), hepatitis C virus (HCV), dengue fever virus, bovine viral diarrhea virus (BVDV), hepatotrophic viruses (hepatitis A virus (HAV), hepatitis B virus (HBV), hepatitis D virus (HDV), hepatitis E virus (HEV), hepatitis G virus (HGV), Crimean-Congo hemorrhagic fever virus (CCHF), bunyaviruses (Punta Toro virus, Rift Valley fever virus (RVFV), and sandfly fever Sicilian virus), Hantaan virus, Caraparu virus), human papilloma viruses, encephalitis viruses (La Crosse virus), arena viruses (Junin and Tacaribe virus), reovirus, vesicular stomatitis virus, rhinoviruses, enteroviruses (polio virus, coxsackie viruses, encephalomyocarditis virus (EMC)), Lassa fever virus, and togaviruses (Sindbis and Semlike forest viruses) and poxviruses (vaccinia virus), adenoviruses, rubiola, and rubella.

According to another embodiment, the term "IMPDH-mediated disease" as used herein includes vascular cellular hyperproliferative diseases such as restenosis, stenosis, artherosclerosis and other hyperproliferative vascular disease.

According to another embodiment, the term "IMPDDH-mediated disease" as used herein includes tumors and malignancies, such as lymphoma, leukemia and other forms of cancer such as breast cancer, prostate cancer, colon cancer, pancreatic cancer, etc.

According to another embodiment, the term "IMPDH-mediated disease" as used herein includes inflammatory diseases such as osteoarthritis, acute pancreatitis, chronic pancreatitis, asthma and adult respiratory distress syndrome.

According to another embodiment, the present invention provides amorphous Compound 1. According to one embodiment, the amorphous form of Compound 1 is produced by converting a crystalline form of Compound 1, e.g., Form A, into an amorphous form of Compound 1.

According to another embodiment, the present invention provides a pharmaceutical composition comprising amorphous form of Compound 1 and a pharmaceutical acceptable adjuvant or carrier.

According to another embodiment, the present invention provides a method of formulating a pharmaceutical composition comprising an amorphous form of Compound 1, comprising the steps of:

(i) converting any one of Form A, Form B, Form C, Form D, Form E or Form F to an amorphous form; and (ii) combining said amorphous form with one or more suitable pharmaceutical carriers or adjuvants.

The above steps may be performed separately or simultaneously to produce the pharmaceutical composition.

According to another embodiment, the amorphous form of Compound 1 is produced from Form E.

Suitable methods for the conversion of a crystalline form, such as a polymorphic form of the present invention, into an amorphous form suitable for formulation are well known in the art. See, e.g., "Remington: The Science & Practice of Pharmacy"; Alfonso R. Gennaro, Editor, Mack Publishing, 1995, 19th Edition, Volume 2, the entire disclosure whereof is incorporated herein by reference.

In order that the invention described herein may be more fully understood, the following examples are set forth. It should be understood that these examples are for illustrative purposes only and are not to be construed as limiting this invention in any manner.

EXAMPLES

Experimental Methods

X-RAY Powder Diffraction

Analyses were carried out on a Shimadzu XRD-6000 X-ray powder diffractometer using Cu K alpha radiation. The instrument was equipped with a long fine focus X-ray tube. The tube voltage and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40°2θ was used. A silicon standard was analyzed to check the instrument alignment. Samples were prepared for analysis by placing them in an aluminum/silicon sample holder.

Differential Scanning Calorimetry (DSC)

Analyses were carried out on a TA Instruments differential scanning calorimeter 2920. The instrument was calibrated using indium as the reference material. The sample was placed into a standard aluminum DSC pan with a crimped lid configuration, and the weight accurately recorded. The sample cell was equilibrated at 25° C. and heated under nitrogen purge at a rate of 10° C./min, up to a final temperature of 350° C. DSC was also used to obtain melting points for the polymorphs.

Example 1

Compound 1 was synthesized using the methods described in the '178 patent.

Abbreviations and terms which are used in the examples that follow include:

EtOAc: ethyl acetate

MEK: methyl ethyl ketone $N_2$: nitrogen gas

L: liter $T_{max}$: maximum temperature

SLS: dodecyl sulfate, sodium salt

Nutsche: nutsche filter

Rosenmund: Rosenmund pressure filter

Kg: kilogram

Preparation of Form A

Compound 1 in ~72 kg of EtOAc (ethyl acetate) was polish filtered, then concentrated under vacuum to a total volume of ~32 L. Toluene (109 kg) was charged to the reactor over 3 h. and the resulting slurry was agitated for several days at ambient temperature, then centrifuged. The filtercake was dried in vacuo with $N_2$ bleed at 50° C. for 20 h. This product (10.89 kg) was dissolved in 20.2 kg of MEK (methyl ethyl ketone) at 70° C. Toluene (83.2 kg) was added and the mixture was slowly cooled to 20° C. where it was agitated for 19 h then centrifuged. The filtercake was dried in vacuo with $N_2$ bleed at 50° C. overnight. The resultant product was slurried with 65 kg of heptane at ambient temperature for 5 hours then centrifuged. The filtercake was dried in vacuo with $N_2$ bleed at 50° C. for 34 hours to produce Form A.

Preparation of Form A

In a 300-gal reactor, Compound 1 (50 kg) was dissolved in 480 L of EtOAc at 70-77° C. and then polish filtered at 30-40° C. This was cooled to 25-30° C. and seeded with 150 g of Form A. The reaction mixture was then concentrated under vacuum at 30-40° C. to a volume of 150 L. The temperature was adjusted to 20-30° C. and stirred for 1 hour such that the batch fully crystallized. To this, 425 L EtOAc was charged and the reaction mixture heated to 40-50° C. Slowly, 575 L heptane was added at 40-50° C. over 1 hour. The reaction mixture was cooled to 20-25° C. over 1-2 hours and stirred at 20-25° C. for 5 hours. The product was filtered on 1 m² Rosenmund and rinsed with 370 L heptane/EtOAc, 1:1. The filtercake was then dried in vacuo with $N_2$ bleed at 45-55° C. for 12 hours to produce Form A.

Preparation of Form A

A suspension of Form B in distilled water was kept stirring or left unstirred at room temperature for 5-10 days. The product was filtered or centrifuged, washed with distilled water (3×) and then vacuum-dried at room temperature to produce Form A.

Preparation of Form A

A suspension of Form B in a 0.001-0.1% weight to volume surfactant solution of SLS was kept stirring or left unstirred at room temperature for 5-10 days. The product was filtered or centrifuged, washed with distilled water (3×) and then vacuum-dried at room temperature to produce Form A.

Preparation of Form B 1.135 kg of Compound 1 was dissolved in 2.4 L of MEK at 65° C. and then polish filtered. To this solution at 65° C. was added 11.5 L of toluene. The mixture was allowed to cool overnight with stirring. The product was filtered and rinsed with toluene, then dried in vacuo with $N_2$ bleed at 50° C. for 5 days. This material was slurried at ambient temperature in 10 vol heptane overnight then filtered, rinsed, and dried in vacuo with $N_2$ bleed at 50° C. overnight. One additional heptane slurry was done to remove the residual toluene. The filtercake was then dried in vacuo with $N_2$ bleed at 50° C. overnight to produce Form B.

Preparation of Form B 2.29 kg of Compound 1 was dissolved in 4.6 L MEK at 60° C. To this solution was added 13.8 L toluene and the mixture was allowed to cool to ambient temperature overnight without stirring. Precipitated solid was stirred for one hour, then filtered and rinsed with toluene. The resulting filtercake was suspended in 23 L of hexanes and refluxed overnight. The suspension was filtered hot and the resulting filtercake rinsed with hexanes. The product was then dried in vacuo with $N_2$ bleed @ 50° C. for several days to give Form B.

Preparation of Form B

Compound 1 was dissolved in trifluoroethanol and Form B was produced by antisolvent crystallization using diethyl ether.

Preparation of Form C

N-propanol and heptane were used in a crash cool procedure on Compound 1. The product formed was vacuum filtered, and allowed to dry to produce Form C.

Preparation of Form D 2.29 kg of Compound 1 was dissolved in 4.6 L MEK at 60° C. To this was added 13.8 L toluene and the solution was allowed to cool to ambient temperature overnight without stirring. The solid was stirred for an hour the next morning, then filtered and rinsed with toluene. The resulting filtercake was suspended in 23 L hexanes and refluxed overnight. This suspension was filtered hot and air dried to give Form D.

Preparation of Form D

Compound 1 was crystallized using evaporation techniques with a nitromethane/toluene solvent system or trifluoroethanol/toluene solvent system. The resultant product was allowed to air dry to produce Form D.

Preparation of Form E

Compound 1 (~115 g) was dissolved in 250 mL MEK at 70° C. At 70° C. 1.0 L of heptane was added and the mixture allowed to cool. The product oiled out and at 30° C. the oil solidified. The suspension was stirred at ambient temperature overnight. The slurry was filtered, rinsed, and pulled dry on the funnel to give From E.

Preparation of Form E

In a 300-gal reactor Compound 1 in EtOAc was concentrated under vacuum at $T_{max}$=40° C. to a total volume of 150-250 L. EtOAc (400 L) was charged to the reactor. The resulting solution was polished filtered, then concentrated under vacuum at $T_{max}$=40° C. to a total volume of 150-200 L. Another 390 L of EtOAc was added and the mixture concentrated under vacuum at $T_{max}$=40° C. to a total volume of 150-200 L which resulted in product precipitation. The mixture was stirred at 20-35° C. for 1 hour, then charged with 424 L of EtOAc. The mixture was warmed to 40-50° C. and 700 L of heptane was added slowly over 2 hours. The mixture was cooled to 15-25° C. over 2 hours, then stirred at the same temperature for 1 hour. The suspension was filtered on a 1 m² filter nutsche then rinsed with 426 L of heptane/EtOAc, 3:1. The resulting filtercake was dried in vacuo with $N_2$ bleed at 45-55° C. for 12 hours to produce Form E.

Preparation of Form E

A suspension of Form B in a 0.1% weight to volume surfactant solution of SLS was kept stirring or left unstirred at room temperature for 5-10 days. The product was filtered or centrifuged, washed with distilled water (3×) and then vacuum-dried at room temperature to produce Form E.

Preparation of Form F

Compound 1 was crystallized using slow cool techniques with an acetone/water solvent system. The resultant product was allowed to air dry to produce Form F.

The invention claimed is:

1. A polymorphic Form A of (1-{3-[3-(4-cyano-3-methoxy-phenyl)ureido]-phenyl}-ethyl)-carbamic acid-2-cyano-1-ethyl-ethyl ester, characterized by one or more peaks at about 5.76, 7.82, 8.10, 10.08, and 15.73 degrees 2θ in an X-ray powder diffraction pattern obtained using Cu K alpha radiation.

2. The polymorphic Form A according to claim 1, wherein said X-ray diffraction pattern is substantially similar to FIG. 1.

3. The polymorphic Form A according to claim 1, wherein said Form A is characterized by a melting point temperature of between 148° C. to about 156° C.

4. A pharmaceutical composition comprising:
   (a) a polymorphic Form according to claim 2; and
   (b) a pharmaceutically acceptable carrier or adjuvant.

5. A process for preparing a polymorph of Form A according to claim 2, said process comprising at least one of the following steps:
   a) dissolving 1-{3-[3-(4-cyano-3-methoxy-phenyl)ureido]-phenyl}-ethyl)-carbamic acid-2-cyano-1-ethyl-ethyl ester in ethyl acetate with agitation at a temperature of 70-77° C. to give a solution;
   b) filtering said solution through a medium at a temperature of 30-40° C. to give a filtrate;
   c) cooling said filtrate to about room temperature;
   d) seeding said filtrate with a quantity of Form A;
   e) concentrating said filtrate under a reduced pressure and at a temperature of 20-30° C. to about one-third the original volume to give a slurry;
   f) agitating said slurry for a period of time at a temperature of 20-30° C.;
   g) adding an amount of a solvent at a temperature of 40-50° C. to generate a solution;
   h) adding about one volume of a solvent over a period of about 1 hour, at a temperature of about 20-25° C. with agitation to generate a slurry;
   i) cooling said slurry to about room temperature and agitating for a period of time;
   j) isolating the product by filtration or centrifugation;
   k) rinsing said product with about a 1:1 mixture of heptane and ethyl acetate; and
   l) drying said product at a temperature of about 45-55° C. under reduced pressure for a period of time to constant weight.

6. A polymorphic Form A, wherein said polymorphic Form A has a peak position at about 5.76 degrees 2θ in an x-ray powder diffraction pattern obtained using Cu K alpha radiation.

7. A polymorphic Form A, wherein said polymorphic Form A has a peak position at about 7.82 degrees 2θ in an x-ray powder diffraction pattern obtained using Cu K alpha radiation.

8. A polymorphic Form A, wherein said polymorphic Form A has a peak position at about 8.10 degrees 2θ in an x-ray powder diffraction pattern obtained using Cu K alpha radiation.

9. A polymorphic Form A, wherein said polymorphic Form A has a peak position at about 10.08 degrees 2θ in an x-ray powder diffraction pattern obtained using Cu K alpha radiation.

10. A polymorphic Form A, wherein said polymorphic Form A has a peak position at about 15.73 degrees 2θ in an x-ray powder diffraction pattern obtained using Cu K alpha radiation.

11. A polymorphic Form A, wherein said polymorphic Form A is characterized by an X-ray diffraction pattern substantially similar to FIG. 1.

* * * * *